United States Patent
Toledano et al.

(10) Patent No.: US 10,702,493 B2
(45) Date of Patent: *Jul. 7, 2020

(54) METHODS AND COMPOSITIONS FOR THE TREATMENT OF ACNE

(71) Applicant: SOL-GEL TECHNOLOGIES LTD., Ness Ziona (IL)

(72) Inventors: Ofer Toledano, Kfar Saba (IL); Ori Nov, Tarum (IL)

(73) Assignee: SOL-GEL TECHNOLOGIES LTD., Ness Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/514,033

(22) Filed: Jul. 17, 2019

(65) Prior Publication Data

US 2019/0336464 A1    Nov. 7, 2019

Related U.S. Application Data

(63) Continuation of application No. 16/033,257, filed on Jul. 12, 2018, now Pat. No. 10,420,743.

(60) Provisional application No. 62/531,396, filed on Jul. 12, 2017.

(51) Int. Cl.
| | | |
|---|---|---|
| *A61K 31/203* | (2006.01) | |
| *A61K 31/327* | (2006.01) | |
| *A61P 17/10* | (2006.01) | |
| *A61K 9/00* | (2006.01) | |
| *A61K 9/50* | (2006.01) | |

(52) U.S. Cl.
CPC ............ *A61K 31/203* (2013.01); *A61K 9/006* (2013.01); *A61K 9/0014* (2013.01); *A61K 9/501* (2013.01); *A61K 31/327* (2013.01); *A61P 17/10* (2018.01)

(58) Field of Classification Search
CPC ...... A61K 31/203; A61K 31/327; A61K 9/00; A61K 9/50; A61P 17/10
See application file for complete search history.

(56) References Cited

U.S. PATENT DOCUMENTS

| | | | |
|---|---|---|---|
| 4,235,872 A | 11/1980 | Tocker | |
| 4,670,250 A | 6/1987 | Baker | |
| 4,671,956 A | 6/1987 | Bouillon et al. | |
| 4,690,825 A | 9/1987 | Won | |
| 4,931,362 A | 6/1990 | Tsifkovits et al. | |
| 4,960,772 A | 10/1990 | Sebag et al. | |
| 4,970,031 A | 11/1990 | Gotoh | |
| 5,145,675 A | 9/1992 | Won | |
| 5,238,714 A | 8/1993 | Wallace et al. | |
| 5,575,987 A | 11/1996 | Kamei et al. | |
| 5,879,716 A | 3/1999 | Katz et al. | |
| 5,955,109 A | 9/1999 | Won | |
| 6,238,650 B1 | 5/2001 | Lapidot et al. | |
| 6,251,313 B1 | 6/2001 | Deubzer et al. | |
| 6,303,149 B1 | 10/2001 | Magdassi et al. | |
| 6,337,089 B1 | 1/2002 | Yoshioka et al. | |
| 6,436,375 B1 | 8/2002 | Lapidot et al. | |
| 6,468,509 B2 | 10/2002 | Lapidot et al. | |
| 6,855,335 B2 | 2/2005 | Seok et al. | |
| 7,629,394 B2 | 12/2009 | Yan | |
| 8,617,580 B2 | 12/2013 | Toledano et al. | |
| 9,205,395 B2 | 12/2015 | Yan | |
| 9,452,137 B2 | 9/2016 | Shevachman et al. | |
| 2002/0064541 A1 | 5/2002 | Lapidot | |
| 2004/0137031 A1 | 7/2004 | Seitz et al. | |
| 2005/0037087 A1 | 2/2005 | Lapidot et al. | |
| 2006/0003014 A1 | 1/2006 | Jadhav et al. | |
| 2010/0029765 A1 | 2/2010 | Gupta et al. | |
| 2010/0180464 A1 | 7/2010 | Laakso et al. | |
| 2012/0202695 A1 | 8/2012 | Toledano et al. | |
| 2013/0095185 A1 | 4/2013 | Toledano et al. | |
| 2014/0136630 A1 | 7/2014 | Schwantes | |
| 2015/0328615 A1 | 11/2015 | Dihora et al. | |

FOREIGN PATENT DOCUMENTS

| | | |
|---|---|---|
| EP | 0248531 A2 | 12/1987 |
| EP | 0934773 A2 | 8/1999 |
| EP | 0941761 A2 | 9/1999 |
| GB | 2416524 A | 2/2006 |
| WO | WO 1993/021764 A1 | 11/1993 |
| WO | WO 1994/020075 | 9/1994 |
| WO | WO 2000/009652 A2 | 2/2000 |
| WO | WO 2000/071084 A1 | 11/2000 |
| WO | WO 2000/072806 A2 | 12/2000 |
| WO | WO 2001/080823 A2 | 11/2001 |
| WO | 2003/003497 A1 | 1/2003 |
| WO | WO 2003/039510 A1 | 5/2003 |
| WO | WO 2003/066209 A1 | 8/2003 |
| WO | WO 2004/081222 A2 | 9/2004 |
| WO | WO 2005/009604 A1 | 2/2005 |
| WO | WO 2009/051839 A1 | 4/2009 |

OTHER PUBLICATIONS

Graber E. "Hormonal therapy for women with acne vulgaris" UpToDAte, Waltham, MA.(Accecsed on Feb. 20, 2016.). 2017.
Yan AC. "Current concepts in acne management" Adolescent medicine clinics. Oct. 2006; 17(3):613-37.
Ziana (clindamycin phosphate 1.2% and tretinoin 0.025%) Gel for topical use only Initial U.S. Approval: 2006 "Highlights of Prescribing Information"; Web access: https://www.accessdata.fda.gov/drugsatfda_docs/label/20061050.8021bl.pdf.
Date, A. A., Naik, B., & Nagarsenker, M. S. (2006). Novel drug delivery systems: potential in improving topical delivery of antiacne agents. Skin Pharmacology and Physiology, 19(1), 2-16.

*Primary Examiner* — Zohren A Fay
(74) *Attorney, Agent, or Firm* — Mark S. Cohen; Pearl Cohen Zedek Latzer Baratz LLP

(57) ABSTRACT

The present application is directed to regimens, methods of treatment, and compositions for the treatment of acne in a subject suffering therefrom.

22 Claims, 1 Drawing Sheet

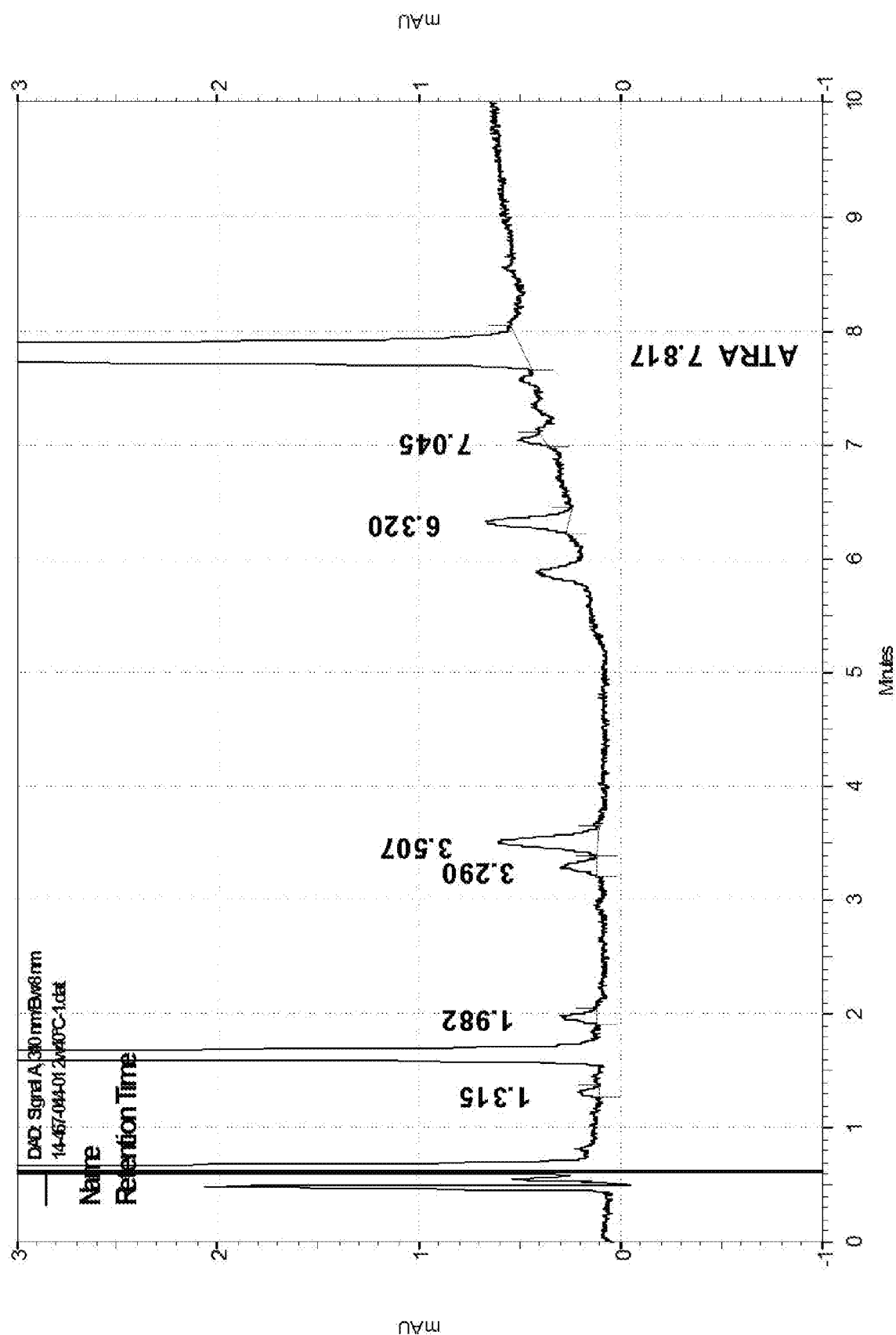

METHODS AND COMPOSITIONS FOR THE TREATMENT OF ACNE

CROSS REFERENCE TO RELATED APPLICATIONS

This Application is a Continuation Application from U.S. application Ser. No. 16/033,257 filed Jul. 12, 2018, which claims the benefit of U.S. Ser. No. 62/531,396, filed on Jul. 12, 2017 which is incorporated in its entirety herein by reference.

FIELD OF THE INVENTION

The present application is directed to regimens, methods of treatment and compositions for the treatment of acne in a subject suffering therefrom.

BACKGROUND OF THE INVENTION

Acne vulgaris is a common condition of the pilo-sebaceous units of the skin (hair follicles and oil glands). Acne is the most common skin disorder in the United States, affecting 40-50 million Americans. Acne usually begins in puberty, but the condition is not restricted to any age group. Approximately 85% of people between the ages of 12 and 24 experience at least minor, most often on the face, chest, and back [Bhate and Williams].

Acne is caused by four major factors: (1) production of oil by enlarged oil glands in the skin, (2) blockage of the hair follicles that release oil, (3) growth of bacteria, called *Propionibacterium acnes* (*P. acnes*), within the hair follicles and (4) inflammatory/immune response to *P. acnes*.

The pathophysiologic features of acne suggest that combination therapy should be utilized as early as possible to simultaneously attack the multiple pathogenic factors of the condition [Gollnick and Cunliffe]. Antimicrobials have been a mainstay of acne treatment for many years, having multiple mechanisms of action. The most important may be the ability of antibiotics to decrease the number of *P. acnes* in and around the follicle. They have a bacteriostatic effect on *P. acnes*, which prevents the bacteria from producing pro-inflammatory molecules [Leyden et al.].

In clinical practice, it is common for physicians to prescribe multiple topical products for acne. Topical products are applied one or two times a day by the patient. However, many of these compounds are irritating with resultant development of facial erythema and discontinuation of the products or noncompliance with therapy. Benzoyl peroxide (BPO) and all trans retinoic acid (ATRA) are two active ingredients with different pharmacological actions that are commonly used for the treatment of acne.

Topical retinoids are keratinization inhibitors. They work by decreasing the cohesiveness of follicular epithelial cells. This, results in an inhibition in the formation of microcomedones, preventing the formation of mature comedones and inflammatory lesions [Gollnick and Cunliffe]. Use of retinoids promotes the normal desquamation of follicular epithelium. The action of the retinoid may enhance the penetration of other topical compounds used to treat acne.

BPO is a commonly used topical antibacterial agent for acne available either by prescription in combinations or over the counter (OTC) BPO has been found to be lethal to *P. acnes* as well as other bacteria that may reside on the skin. So far there has been no indication of any bacteria developing a resistance to BPO. It has also been demonstrated that BPO has keratolytic activity contributing to its efficacy in treating comedonal acne [Tanghetti]. BPO reduces the cohesiveness of the cells of the stratum corneum, thus improving topical drug delivery through the epidermal barrier.

Silica microcapsule systems have been developed to overcome many of the limitations (such as degradation and irritation) of standard pharmaceutical formulations involving multiple active ingredients. The encapsulation of active ingredients in silica microcapsules serves to protect components in the formulation from interacting with one another and, as a consequence, increases overall formulation stability. Silica is chemically inert, photochemically and physically stable, and safe for topical use.

Applicant's silica encapsulated products meet the criteria for categorical exclusion defined in 21 CFR 25.31(e), and that to the knowledge of Applicant, no extraordinary circumstances exist as defined in 21 CFR 25.21. Thus, no environmental assessment is required according to 21 CFR 25.20(1). For the case of encapsulated BPO (E-BPO)/encapsulated ATRA (E-ATRA), microencapsulation of both BPO and tretinoin protects the tretinoin from oxidative decomposition by BPO, thereby enhancing the stability for this novel combination product and ensuring a suitable clinical and commercial shelf life (U.S. Pat. No. 8,617,580 and US 2012/0202695).

Clinicians have been reluctant to prescribe topical retinoids and BPO concurrently due to a belief that the BPO may result in oxidation and degradation of the tretinoin molecule, thereby reducing its effectiveness, and prefer to recommend the BPO or an antibiotic/BPO combination to be applied in the morning and tretinoin at night (Yan A C. Current concepts in acne management. Adolesc. Med. Clin. 2006; 17(3):613-637.)

Another publication (Emmy Graber, Treatment of Acne Vulgaris, UpToDate.com, July 2016) states "topical tretinoin should NOT be applied at the same time as benzoyl peroxide", despite the known fact that newer retinoid compositions like Retin A microspheres (MICROSPONGE® System) have less interaction or no short term interaction with BPO. Obviously, concomitant administration of tretinoin and BPO is taught away by this publication.

Unlike adapalene, which is often combined with BPO, tretinoin is significantly more irritant to the skin and since BPO is also irritant, it has been feared that the two APIs together will create unacceptable cutaneous side effects. Also, BPO is known to oxidize tretinoin and hence it was feared that their interaction on the skin when administered together will diminish the therapeutic effect of tretinoin. Thus, while there are some reports in the literature on the value of both compounds being administered one in the morning and the other in the evening, the verdict up to now was that the two products should not be administered concomitantly.

This belief of the medical profession explains why all previous attempts to solve the stability problem of tretinoin/BPO, such as microencapsulation technology, did not yield a commercial product so far.

Combination topical therapy is the recommended standard of care for the management of patients with acne [Gollnick and Cunliffe]. Combination therapy targets multiple pathogenic factors: abnormal follicular keratinization, *P. acnes* proliferation and inflammation. Combining the separate product applications into a single delivery system would provide the patient with the convenience of a single product, thus improving patient adherence and improving treatment outcomes.

SUMMARY OF THE INVENTION

In some embodiments, this invention provides a method of treating acne comprising: topically applying onto an affected skin area of a subject in need thereof once a day for a period of time of up to 12 weeks, a topical medicament which comprises the active agents:

Tretinoin or a pharmaceutically acceptable salt thereof in an amount of about 0.1% weight; and Benzoyl Peroxide in an amount of about 3% weight.

In some embodiments, in the method of this invention, the score of at least one parameter evaluated by an Investigator Cutaneous Safety Assessment is synergistically lower than the score of the parameters evaluated with the same treatment regimen with each of the active agents separately. In another embodiment, the at least one parameter evaluated by the Investigator Cutaneous Safety Assessment is selected from Erythema, Scaling, Pigmentation and any combinations thereof.

In some embodiments, in the method of this invention, the score of at least one parameter evaluated by a Local Tolerability Score is synergistically lower than the score of the parameters evaluated with the same treatment regimen with each of the active agents separately. In another embodiment, the at least one parameter evaluated by the Local Tolerability score is selected from Itching, Burning, Stinging, and any combinations thereof.

In some embodiments, in the method of this invention, the method reduces at least one of:
(i) the number of inflammatory acne lesions by at least 50%; or
(ii) the number of non-inflammatory acne lesions by at least 40%.

In other embodiments, the method reduces the number of inflammatory acne lesions by at least 50%; and the number of non-inflammatory acne lesions by at least 40%.

In other embodiments, the method improves the IGA success rate by at least 20% compared to the baseline score.

In other embodiments, in the method of this invention, the score of at least one efficacy parameter is synergistically higher than the parameter evaluated with the same treatment regimen with each of the active agents separately. In another embodiment, the efficacy parameter is selected from at least one of IGA success rate, mean reduction in inflammatory lesions count, mean reduction in non-inflammatory lesion count, mean reduction in acne symptom domain, mean reduction in acne impact domain and mean reduction in verbal rating scale.

In other embodiments, in the method of this invention, after two weeks storage at 40° C. of the topical medicament, the concentration of all-trans 5,6-epoxy retinoic acid is lower than 1%. In other embodiments, in the method of this invention, after two weeks storage at 40° C. of the topical medicament, the degradation of said tretinoin is less than 2.5%.

In other embodiments, in the method of this invention, the method potentiates the action of tretinoin in the treatment of acne.

In other embodiments, in the method of this invention, the release rate of said tretinoin from said topical medicament is less than 60% per h. In other embodiment, the release rate of said tretinoin from said topical medicament is less than 60% per h in a medium of 70% IPA (isopropyl alcohol) and 30% water at room temperature.

In other embodiments, in the method of this invention, the at least one active agent of said medicament is encapsulated in a shell. In another embodiment, both active agents, BPO and Tretinoin, of the medicament are encapsulated in a shell. In another embodiment, the shell is a metal oxide or semi-metal oxide inorganic shell.

In other embodiments, the topical medicament in a single dose medicament comprising both said active agents.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1 shows the HPLC chromatogram of an embodiment composition of the invention comprising 0.05% E-ATRA and 3% E-BPO eluted with acetonitrile and acetic acid 1% in water on a Zorbax RX-C18 3.5 mμ, 4.675 mm column, showing the RRT 0.44 product (all-trans 5,6-epoxy retinoic acid) at retention time of about 3.5 min (RRT product calculated relative to the ATRA peak at 7.8 min).

DETAILED DESCRIPTION OF THE PRESENT INVENTION

In the first aspect, the present invention provides a regimen for the treatment of acne comprising: topically applying onto an affected skin area of a subject in need thereof, once a day for a period of time of up to 12 weeks, a topical medicament which comprises the active agents:

Tretinoin or a pharmaceutically acceptable salt thereof, in an amount of between about 0.05% to about 0.1% weight; and Benzoyl Peroxide in an amount of at least about 3% weight.

In a further aspect, the present invention provides a regimen for the treatment of acne comprising: topically applying onto an affected skin area of a subject in need thereof, once a day for a period of time of up to 12 weeks, a topical medicament which comprises the active agents:

Tretinoin or a pharmaceutically acceptable salt thereof, in an amount of between about 0.05% to about 0.1% weight; and Benzoyl Peroxide in an amount of at least about 3% weight;

wherein the score of at least one parameter evaluated by an Investigator Cutaneous Safety Assessment is synergistically lower than the score of the parameters evaluated with the same treatment regimen with each of the active agents separately. In another embodiment, the topical medicament comprises about 0.1% tretinoin and about 3% benzoyl peroxide.

In some embodiments, the at least one parameters evaluated by the Investigator Cutaneous Safety Assessment is selected from Erythema, Scaling, Pigmentation and any combinations thereof.

In yet another aspect, the present invention provides a regimen for the treatment of acne comprising: topically applying onto an affected skin area of a subject in need thereof, once a day for a period of time of up to 12 weeks, a topical medicament which comprises the active agents:

Tretinoin or a pharmaceutically acceptable salt thereof, in an amount of between about 0.05% to about 0.1% weight; and Benzoyl Peroxide in an amount of at least about 3% weight;

wherein the score of at least one parameter evaluated by a Local Tolerability Score is synergistically lower than the score of the parameters evaluated with the same treatment regimen with each of the active agents separately. In another embodiment, the topical medicament comprises about 0.1% tretinoin and about 3% benzoyl peroxide.

In some embodiments, the at least one parameter evaluated by the Local Tolerability score is selected from itching, burning, stinging, and any combinations thereof.

In a further aspect, the present invention provides a regimen for the treatment of acne comprising: topically applying onto an affected skin area of a subject in need thereof, once a day for a period of time of up to 12 weeks, a topical medicament which comprises the active agents:
Tretinoin or a pharmaceutically acceptable salt thereof, in an amount of between about 0.05% to about 0.1% weight; and
Benzoyl Peroxide in an amount of at least about 3% weight;
wherein said regimen improves the IGA success rate by at least 20% compared to the baseline score. In another embodiment, the topical medicament comprises about 0.1% tretinoin and about 3% benzoyl peroxide.

In some embodiments, said regimen improves the IGA success rate by reducing the number of acne lesions and improving the clinical condition of a patient in need thereof as compared to their baseline condition/score.

In another one of its aspects, the present invention provides a regimen for the treatment of acne, comprising topically applying onto an affected skin area of a subject in need thereof, once a day for a period of time of up to 12 weeks, a topical medicament which comprises tretinoin or a pharmaceutically acceptable salt thereof as a single active agent in an amount of between about 0.05% to about 0.1% weight; wherein said active agent is encapsulated in a shell; and
wherein the score of at least one parameter evaluated by an Investigator Cutaneous Safety Assessment is lower than the score of the parameters evaluated with the same treatment regimen using a non-encapsulated active agent. In another embodiment, the topical medicament comprises about 0.1% tretinoin and about 3% benzoyl peroxide.

In a further aspect, the present invention provides a regimen for the treatment of acne, comprising topically applying onto an affected skin area of a subject in need thereof, once a day for a period of time of up to 12 weeks, a topical medicament which comprises tretinoin or a pharmaceutically acceptable salt thereof, as a single active agent in an amount of between about 0.05% to about 0.1% weight; wherein said active agent is encapsulated in a shell; and
wherein the score of at least one parameter evaluated by Local Tolerability Score is lower than the score of the parameters evaluated with the same treatment regimen using a non-encapsulated active agent. In another embodiment, the topical medicament comprises about 0.1% tretinoin and about 3% benzoyl peroxide.

In some embodiments, the amount of said encapsulated tretinoin is about 0.1% weight.

In another one of its aspects, the present invention provides a regimen for the treatment of acne comprising: topically applying onto an affected skin area of a subject in need thereof, once a day for a period of time of up to 12 weeks, a topical medicament which comprises the active agents:
Tretinoin or a pharmaceutically acceptable salt thereof, in an amount of between about 0.05% to about 0.1% weight; and
Benzoyl Peroxide in an amount of at least about 3% weight;
wherein said regimen reduces at least one of:
(i) the number of inflammatory acne lesions by at least 50%; or
(ii) the number of non-inflammatory acne lesions by at least 40%.

In another embodiment, the topical medicament comprises about 0.1% tretinoin and about 3% benzoyl peroxide. In another embodiment, the topical medicament used in the regimen treatment or method of treatment of this invention is described in US patent publication 2013/0095185, which is incorporated herein by reference.

In some embodiments, the amount of said tretinoin is about 0.1% weight and the amount of said benzoyl peroxide is at least about 3% weight. It should be noted that the composition having these active agents in these concentrations was shown to have unexpected and surprising benefits with respect to the tolerability of the product (less side effects such as burning and itching, stinging and so forth), safety of the treatment (less erythema, scaling, pigmentation and so forth), and effectiveness of the treatment of acne (treatment with the composition following the regimen of the invention significantly reduced the number of non-inflammatory and inflammatory acne lesions). Surprisingly, when increasing the concentration of the tretinoin from 0.05% to 0.1%, while the efficacy increased, the side effects were not increased and in some cases were even reduced. For example, 44.8% subjects complained about burning side effects at 12 weeks of using the composition comprising 0.05% tretinoin and 3% benzoyl peroxide (see Table 21), while only 38.1% subjects complained about burning side effect when increasing the concentration of the tretinoin to 0.1% (see Table 18).

In some embodiments said regimen reduces the number of non-inflammatory acne lesions by at least 40%. In other embodiments, said regimen reduces the number of inflammatory acne lesions by at least 50%. In yet further embodiments, said regimen reduces the number of inflammatory acne lesions by at least 50%; and the number of non-inflammatory acne lesions by at least 40%.

In some embodiments, after two weeks storage at 40° C. of the topical medicament of the invention, the concentration of RRT (relative retention time) 0.44, (all-trans 5,6-epoxy retinoic acid, that is the major tretinoin degradation product) is lower than 1%. In other embodiments, after two weeks storage at 40° C. of the topical medicament of the invention, the degradation of said tretinoin is less than 2.5%.

When referring to RRT 0.44 it should be understood to relate to the degradation product of tretinoin in the presence of BPO as shown in the HPLC chromatography of the composition of the invention after two weeks of storage at 40° C. An example of the RRT product can be seen in FIG. 1 at retention time 3.507 min. In other embodiments, RRT 0.44 refers to all-trans 5,6-epoxy retinoic acid represented by the following structure:

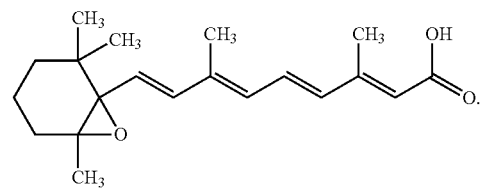

The invention further provides a method of treating acne, comprising topically applying onto an affected skin area of a subject in need thereof, once a day for a period of time of up to 12 weeks, a topical medicament which comprises of the active agents: Tretinoin or a pharmaceutically acceptable salt thereof, in an amount of between about 0.05% to about 0.1% weight; and Benzoyl Peroxide in an amount of at least about 3% weight; wherein said method potentiates the action of tretinoin in the treatment of acne.

The present invention further provides a regimen for the treatment of acne comprising: topically applying onto an affected skin area of a subject in need thereof, once a day for a period of time of up to 12 weeks, a topical medicament which comprises the active agents: Tretinoin or a pharmaceutically acceptable salt thereof, in an amount of between about 0.05% to about 0.1% weight; and Benzoyl Peroxide in an amount of at least about 3% weight; wherein the release rate (dissolution rate) of said tretinoin from said topical medicament is less than 60% per h. In some embodiments, the release rate (dissolution rate) of said tretinoin from said topical medicament is less than 50% per h. In some embodiments, the release rate (dissolution rate) of said tretinoin from said topical medicament is less than 45%, 40%, 35%, 30% or 25% per h.

It should be noted that the release rate (dissolution rate) defined herein relates to the measurement (either in vitro or in vivo) of the rate at which the active agents (for example tretinoin) is released from the topical medicament of the invention, to the extracting media or skin. The release rate is measured using known methods, such as for example: (1) 70% IPA (isopropyl alcohol) and 30% water and optionally an antioxidant (such as BHT) at room temperature; (2) 60-80% alcohol, ACN (acetonitrile) at room temperature; or (3) 2% Tween 80, IPA in a ratio of 2:1, and optionally an antioxidant (such as BHT) at 32° C.

In some embodiments, said release rate of said tretinoin from said topical medicament is less than 60% per h in a medium of 70% IPA (isopropyl alcohol) and 30% water at room temperature.

The invention further provides a regimen for the treatment of acne comprising: topically applying onto an affected skin area of a subject in need thereof, once a day for a period of time of up to 12 weeks, a topical medicament which comprises the active agents:
  Tretinoin or a pharmaceutically acceptable salt thereof, in an amount of between about 0.05% to about 0.1% weight; and
  Benzoyl Peroxide in an amount of at least about 3% weight;
  wherein the score of at least one efficacy parameter is synergistically higher than the parameter evaluated with the same treatment regimen with each of the active agents separately. In another embodiment, the topical medicament comprises about 0.1% tretinoin and about 3% benzoyl peroxide.

In some embodiments of regimen of the present invention, said Benzoyl Peroxide is in an amount of about 3% weight. In other embodiments of regimen of the present invention, said Benzoyl Peroxide is in an amount of about 6% weight. In further embodiments of regimen of the present invention, said Benzoyl Peroxide is in an amount of between about 3% to about 6% weight. In yet further embodiments of regimen of the present invention, said Benzoyl Peroxide is in an amount of about 3%, 4%, 5% or 6% weight.

In some embodiments, said efficacy parameter is selected from at least one of IGA success rate, mean reduction in inflammatory lesions count, mean reduction in non-inflammatory lesion count, mean reduction in acne symptom domain (measured using a patient reported outcome study and including symptoms such as for example number of pimples, whiteheads, blackheads, redness), mean reduction in acne impact domain (measured using a patient reported outcome study and including symptoms such as for example sadness, embarrassment, self-consciousness) and mean reduction in verbal rating scale.

As used herein the term "a regimen for the treatment of acne" is used herein interchangeably with the term "method of treating acne" having all the same meaning and qualities. The term "regimen" as used herein should be understood to relate to a medical treatment regimen regulating the treatment of acne in a subject suffering therefrom, including the regulation of the medicament administered (fixed dose combination of the active agents: tretinoin or a pharmaceutically acceptable salt thereof and BPO), the frequency of administration (i.e. once a day), the duration of treatment (i.e. up to 12 weeks), the method of administration (i.e. topical) and the location of administration (i.e. topically applying onto an affected skin area).

When relating to the treatment of "acne" it should be understood to relate to the treatment of a skin condition or disease also known as acne vulgaris in any form or place of its occurrence or severity (mild, moderate, severe or any combinations thereof. In some subjects parts of area of the skin may be mildly inflicted while other area of the skin of the same individual may be severely inflicted). Mild acne is classically defined as open (blackheads) and closed (whiteheads) clogged skin follicles (comedones) limited to the face with occasional inflammatory lesions. Acne may be considered to be of moderate severity when a higher number of inflammatory papules and pustules occur on the skin. Severe acne is said to occur when nodules are the characteristic facial lesions, and involvement of other areas of the body is extensive. Inflammatory acne lesions include papule lesions (small, solid elevation less than 5 mm in diameter, most of the lesion is above the surface of the skin), pustule lesions (small circumscribed elevation less than 5 mm in diameter that contains yellow-white exudate), nodule lesions (inflammatory lesion greater than or equal to 5 mm in diameter) and cyst lesions (inflammatory lesion that contains yellow-white exudate that is greater than or equal to 5 mm in diameter). Non-inflammatory lesions include open comedone (black head)) (lesion in which the follicle opening is widely dilated with the contents protruding out onto the surface of the skin, with compacted melanin cells giving the plug a black appearance) and closed comedone (white head) (lesion in which the follicle opening is closed, but the sebaceous gland is enlarged by the pressure of the sebum buildup, which in turn cause the skin around the follicle to thin and become elevated with a white appearance).

The term "synergistically lower" as used herein should be understood to relate to the degree of lowering the side-effects (as measured using Investigator Cutaneous Safety Assessment and Local Tolerability Score) caused by topical administration of the active agents in a regimen of the invention, as compared with the sum of the side-effects resulting from administration of each of the agents separately.

The term "synergistically higher" as used herein should be understood to relate to the degree of therapeutic efficacy (as measured using efficacy results selected from at least one of IGA success rate, mean reduction in inflammatory lesions count, mean reduction in non-inflammatory lesion count; and/or PRO results selected from at least one of mean reduction in acne symptom domain, mean reduction in acne impact domain and mean reduction in verbal rating scale) caused by topical administration of the active agents in a regimen of the invention, as compared with the sum of the effect resulting from administration of each of the agents separately.

The synergistic lower side-effect of the regimen of the invention is calculated according to the following formula:

$$(TWIN-V) < (ATRA-V) + (BPO-V)$$

TWIN—side effect (using the score measurement indicated above and below) measured for the medicament defined in the present invention.

V—side effect (using the score measurement indicated above and below) measured for the vehicle alone.

ATRA—side effect (using the score measurement indicated above and below) measured for ATRA alone.

BPO—side effect (using the score immurement indicated above and below) measured for BPO alone.

When the effect of the medicament of the invention is measured, the side-effect of the vehicle (V) is subtracted from the side-effect of the medicament (TWIN), the net side-effect of the medicament of the invention (TWIN−V) is numerically lower than the sum of the net clinical benefits of each of the individual active agent after subtraction of the vehicle effect from the ATRA and BPO branches, respectively.

The synergistic higher effect of the regimen of the invention is calculated according to the following formula:

$$(TWIN-V) > (ATRA-V) + (BPO-V)$$

TWIN—therapeutic effect (using the score measurement indicated above and below) measured for the medicament defined in the present invention.

V—therapeutic effect (using the score measurement indicated above and below) measured for the vehicle alone.

ATRA—therapeutic effect (using the score measurement indicated above and below) measured for ATRA alone.

BPO—therapeutic effect (using the score measurement indicated above and below) measured for BPO alone.

When the effect of the medicament of the invention is measured, the therapeutic effect of the vehicle (V) is subtracted from the therapeutic effect of the medicament (TWIN), the net therapeutic effect of the medicament of the invention (TWIN−V) is numerically higher than the sum of the net clinical benefits of each of the individual active agent after subtraction of the vehicle effect from the ATRA and BPO branches, respectively.

It is to be noted that the effect of the regimen of the invention, wherein the two active agents are administered in combination is at least an additive effect and preferentially a synergistic effect. In some embodiments, the synergistic effect refers to the synergistic lowering of the side effects caused by administration of the active agents. In some other embodiments, the additive effect of the regimen of the invention is attributed to the clinical therapeutic effect of the active agents. In further embodiments, the synergistic effect of the regimen of the invention is attributed to the clinical therapeutic effect of the active agents.

It is further noted that any of the above synergistic effects can be attributed to the effect at—at least one of week 2, 4, 8, 12 of the regimen of the invention. In some embodiments, the synergistic effect is provided at week 4 of the regimen of the invention. In some embodiments, the synergistic effect is provided at week 8 of the regimen of the invention. In some embodiments, the synergistic effect is provided at week 12 of the regimen of the invention.

When referring to "improvement", "improves" and any other lingual derivatives of the term it should be understood to include an additive or synergistic therapeutic effect of the regimen of the invention. When referring to "improvement of the IGA success rate by at least 20%" it should be understood to relate to an additive or, in some embodiment synergistic, improvement of the Investigational Global Assessment (IG) success rate measured for degree of success in reducing the number of acne lesions and an improvement in the clinical condition of patients compared to their baseline condition/score.

The term "potentiates the action of tretinoin in the treatment of acne" should be understood to encompass any therapeutic augmentation of the treatment of acne achieved by administering tretinoin to a subject suffering from acne. The therapeutic effect of administering a topical medicament comprising both tretinoin and benzoyl peroxide is either additive or synergistic to the effect of acne treatment with tretinoin alone.

In some embodiments, said medicament is applied at least twice a day. In some further embodiments, said medicament is applied once a day. In some further embodiments, said medicament is applied twice a day. In other embodiments, said medicament is applied twice a day with a period of at least 8 hours between administrations. In some embodiments, said medicament is applied every other day.

In some embodiments, said medicament is administered for a period of up to 12 weeks. In some embodiments, said medicament is administered for a period of 12 weeks. In other embodiments, said medicament is administered for a period of 1 week. In some embodiments, said medicament is administered for a period selected from 1, 2, 4, 8 and 12 weeks.

In some embodiments, said amount of said tretinoin or said pharmaceutically acceptable salt thereof, is at least 0.05% weight.

In other embodiments, said amount of said tretinoin or said pharmaceutically acceptable salt thereof, is about 0.1% weight.

In some embodiments, said medicament is administered in a single composition, single fixed dose medicament, comprising both said active agents (BPO and ATRA). In such embodiments, the weight % of the active agent relates to their weight amount in the single composition. The term "fixed dose medicament" should be understood as meaning a combination whose active agents are combined at fixed doses in the same vehicle (single formula) that delivers them together to the point of application.

In further embodiments, said medicament comprises two separate compositions each one comprising each of said active agents. In such embodiments, the weight % amount of each active agent relates to each of their weight amount in each composition separately. In some embodiments, said two separate compositions of said medicament are administered concomitantly. In further embodiments, said two separate compositions are administered sequentially.

In some embodiments, at least one of said active agents in a medicament disclosed hereinabove is encapsulated in a shell. In some other embodiments, both active agents, BPO and Tretinoin, of said medicament are encapsulated in a shell. In some embodiments, said shell is an inorganic shell. In further embodiments, said encapsulating shell is a metal oxide or semi-metal oxide inorganic shell.

As used herein unless otherwise indicated the term "microcapsule" refers to a microparticle having a core shell structure, wherein said core comprises an active agent as defined herein (core material), being coated by a shell forming the microcapsule entrapping the core. In some embodiments, the coating/shell is directly deposited on the core material. In some embodiments, the core material is solid. In other embodiments, the core material is semi-solid. In some embodiments, the core material consists of a solid particle of the active agent. In other embodiments, the core material comprises a solid particle of the active agent. In some other embodiments, the core material is in a liquid/oily phase.

The size of the microcapsules (denoted herein also by the general term "particles" or "microparticles") as will be referred to herein refers to $D_{90}$ meaning that 90% of the particles have the stated dimension or less (measured by volume). Thus, for examples, for spherical particles stated to have a diameter of 10 micrometers ("microns"), this means that the particles have a $D_{90}$ of 10 microns. The $D_{90}$ (termed also d(0.9)) may be measured by laser diffraction. For particles having a shape other than spheres, the $D_{90}$ refers to the mean average of the diameter of a plurality of particles.

In some embodiments, the microcapsules are formed using the process as disclosed in the following documents (herein incorporated by reference): U.S. Pat. Nos. 6,303,149, 6,238,650, 6,468,509, 6,436,375, US2005037087, US2002064541, and International publications Nos. WO 00/09652, WO00/72806, WO 01/80823, WO 03/03497, WO 03/039510, WO00/71084, WO05/009604, and WO04/81222, disclose sol-gel microcapsules and methods for their preparation; EP 0 934 773 and U.S. Pat. No. 6,337,089 teach microcapsules containing core material and a capsule wall made of organopolysiloxane, and their production; EP0941 761 and U.S. Pat. No. 6,251,313 also teach the preparation of microcapsules having shell walls of organopolysiloxane; U.S. Pat. No. 4,931,362 describes a method of forming microcapsules or micromatrix bodies having an interior water-immiscible liquid phase containing an active, water-immiscible ingredient. Microcapsules prepared by a sol-gel process are also disclosed in GB2416524, U.S. Pat. No. 6,855,335, WO03/066209.

According to some embodiments of the present invention, the coated form of the active ingredient (microcapsule) may be in form of a polymeric microsponge/silica microsphere where the active ingredient is adsorbed, embedded, impregnated or entrapped in the microsponge/silica microsphere as described for example in U.S. Pat. Nos. 4,690,825; 5,145,675, 5,879,716, 5,955,109, and U.S. Pat. No. 9,452,137 incorporated herein by reference in their entirety.

In other embodiments, microcapsules are formed by the encapsulation process disclosed in the following publications (herein incorporated by reference): U.S. Pat. Nos. 7,629,394, 9,205,395, US 2015/0328615, US 2014/0186630. Controlled release microcapsules: IN01958CH2007, IN02080CH2007, U.S. Pat. Nos. 4,235,872, 4,670,250, EP 0248531, U.S. Pat. Nos. 4,970,031, 5,238,714, WO9321764, U.S. Pat. No. 5,575,987, WO9420075, US 2004/137031, US 2006/003014, US 2010/180464.

The core (wherein it is a solid particulate matter) may be of any shape for example r k plate-like, ellipsoidal, cubic, or spherical shape.

In the case of cores having a spherical shape, the diameter ($D_{90}$) may be in the range of 0.3 to 90 microns, in some embodiments 0.3 to 50 microns, in some further embodiments 1 to 50, in some further embodiments 5 to 30 microns.

By the term "the diameter (D90) may be in the range of 0.3 to 90 microns" is meant that 90% by volume of the particles (in this case the particle's core) may be less than or equal to a value in the range of 0.3 to 90 microns.

For generally cubic-shaped cores or cores having a shape resembling that of a cube, the mean size of a side may be in the range 0.3 to 80 microns, in some embodiments 0.3 to 40 microns, in some further embodiments 0.8 to 40 microns, in some further embodiments 4 to 15 microns.

For rod-like shaped, ellipsoidal-shaped and plate-like shaped cores, the largest dimension (that of the longest axis) is typically in the range 10 to 100 microns, in some embodiments 15 to 50 microns; and the smallest dimension is typically in the range 0.5 to 20 microns and in some further embodiments 2 to 10 microns.

According to an embodiment of the present invention, the microcapsules (coated particulate matter) have a diameter (d90) of 0.5 to 100 µm or in some embodiments the diameter of the microcapsules is in the range of 1 to 50 µm and in some other embodiments in the range of 5 to 30 µm. It is appreciated that the microcapsules of the present invention are composed of distinct regions of the metal oxide layer in the core material (i.e. the water insoluble particulate matter).

Further according to an embodiment of the present invention the obtained metal oxide coating layer has a width (thickness) of 0.1 µm or above, in some embodiments the metal oxide coating layer has a width (thickness) of 0.1-10 µm.

Additionally, according to an embodiment of the present invention the obtained metal oxide coating layer has a width (thickness) of 0.3 µm or above, in some embodiments the metal oxide coating layer has a width of 0.3-10 µm.

Additionally, according to an embodiment of the present invention, the thickness of the metal oxide layer is in the range of 0.1-10 µm. In some further embodiments, the thickness of the metal oxide layer is in the range of 0.1-3 µm, and in some further embodiments in the range of 0.1-1 µm. The thickness of the metal oxide layer may also be in some embodiments in the range of 0.3 to 3 µm, and in some other embodiments in the range of 0.3 to 2 µm.

Further according to an embodiment of the present invention the obtained metal oxide coating layer has a width (thickness) of about 0.1, 0.2, 0.3, 0.5, 0.7, 1, 1.5, 2 or 5 µm or above, in some embodiments up to 10 µm.

The width of the metal oxide layer may be determined for example by a Transmission Electron Microscope or Confocal Microscope such that in a circular cross-sectional area of the particle the smallest width is at least e.g. 0.1 µm (the width is determined as the smallest distance from the surface of the particle (i.e. metal oxide surface) to the core-metal oxide interface).

The microcapsules are in some embodiments characterized in that the core material is substantially free of the metal oxide and further in that the metal oxide layer is substantially free of the core material, e.g. either as particle dispersion (in the nano-metric range of below 0.1 µm) of the particulate matter or as molecular dispersion of the particulate matter.

Thus, according to an embodiment of the present invention, the metal oxide layer is substantially free of core material (either in the form of molecules or as nano-metric particles). The term "substantially free" in this context denotes that the concentration of the molecules of the core material or the concentration of the nano-metric particles of the core material is negligible as compared to the metal oxide. Similarly, by the term "the core material is substantially free of the metal oxide" is meant that the concentration of the metal oxide in the core is negligible as compared to the core material. The microcapsules (i.e. first microcapsules) are in some embodiments non leaching when dispersed in a carrier and in some other embodiments non leaching in an aqueous based carrier.

According to another embodiment when the microcapsules are prepared by a method such as spray drying, the core material comprising the active agent may further comprise up to about 30% in some embodiments up to about 20% metal oxide and the metal oxide coating layer may further comprise up to about 30% w/w, in some embodiments up to about 20% w/w of the active agent.

By the term "non-leaching" it is meant that the leaching of the particulate matter (active agent) from the particles into an aqueous-based liquid is less than 5% w/w, in some embodiments less than 3%, in some further embodiments less than 1% w/w in some further embodiments less than 0.5% w/w, and in some other embodiments less than 0.1% w/w at room temperature (20° C.), under gentle agitation for 1 hour or until a steady state concentration is achieved. Typically, the aqueous-based liquid is water. The values indicated above refer to the percentage of the active agent leached into an aqueous medium relative to the initial amount of the active agent in the particles. The leaching values indicated above refer in some embodiments to a dispersion having a concentration of the particulate matter in the aqueous medium higher than 0.1% w/w, in some further embodiments higher than 1% w/w, in some further embodiments higher than 3% w/w, and in some other embodiments higher than 10% w/w. For tretinoin the leaching values indicated above refer in some embodiments to a dispersion having a concentration of the particulate matter in the aqueous medium higher than 0.01% w/w.

According to an embodiment of the present invention the weight ratio of the metal oxide to the solid particulate matter is in the range of 1:99 to 50:50. The weight ratio of the metal oxide layer to the solid particulate matter may be also in the range of 3:97 to 50:50, 5:95 to 50:50, 10:90 to 50:50, 5:95 to 30:70, 10:90 to 30:70. Further, according to an embodiment of the present invention the rate ratio of the metal oxide to the solid particulate matter is in the range of 10:90 to 20:80.

According to another embodiment of the present invention, when spray drying method is used, the weight ratio of the metal oxide to the solid particulate matter may be in the range 5:95 to 95:5.

As used herein by the term "uncoated free form" is meant that the active ingredient (BPO or tretinoin) is present in the composition in its "naked" form meaning that it is not intimately embedded, encapsulated, entrapped or encased in a polymeric carrier, and is present in the composition in direct contact with the composition carrier. As used herein by the term "coated form of the active ingredient" is meant that the active ingredient is embedded, dispersed, entrapped, or encased, e.g. as a solid dispersion or molecular dispersion in a polymeric carrier which may be an organic or inorganic carrier and which may serve as a matrix for dispersing the active ingredient or as encapsulated material coating said active ingredient (i.e. the active ingredient is present in a core or is a core material encapsulated by a shell composed of a polymeric material which may be an organic or inorganic polymer).

According to another embodiment of the present invention, the coated form of the active ingredient is second microcapsules comprising a solid particulate matter of the active ingredient coated by a metal oxide layer.

Further, according to an embodiment of the present invention, the first microcapsules comprise a solid particulate matter of BPO coated by a metal oxide layer.

According to an embodiment of the present invention, the BPO is in the form of first microcapsules comprising solid particulate matter of BPO coated by a metal oxide layer and the tretinoin is in the form of second microcapsules comprising a solid particulate matter of the tretinoin coated by a metal oxide layer.

Under these embodiments, the metal oxide coating layer is advantageous since it is capable of isolating the particulate matter of the active agent from its surrounding medium, thus preventing cross-reactivity of the active agents present in the same composition and yet enables the release the particulate matter upon application to the surface to be treated.

The term "solid water insoluble agent" refers to a solid material having solubility in water of less than 3% w/w, typically less than 1% and at times less than 0.5% w/w at room temperature (20° C.). The "solid water insoluble agent" may have a solubility of less than 0.1% w/w.

The "solid water insoluble agent" may also be termed herein as "solid water insoluble particulate matter" or "solid particulate matter".

The term "topical medicament" as used herein (also referred to as "composition") should be understood to encompass any pharmaceutical formulation that enables the administration of the active agents to a skin tissue of a patient administered with said medicament. The composition or topical medicament of the present invention comprises a carrier. According to an embodiment of the present invention the carrier is in the form of an ointment, a cream, a lotion, an oil, a solution (in some embodiments an aqueous solution), an emulsion, a gel, a paste, a milk, an aerosol, a powder, or a foam. In some embodiments the carrier is an aqueous-based carrier (such as a gel, oil-in water emulsion or oil-in water cream, aqueous solution, foam, lotion, spray).

Thus, the final form of the composition may be any of the above forms, mentioned with respect to the carrier, where the microcapsules are dispersed in the carrier. The final form of the composition may also be in the form of a wash or cleanser.

In some embodiments, the metal oxide is selected from silica, titania, alumina, zirconia, ZnO, and mixtures thereof. In some other embodiments the metal oxide is silica.

Moreover, according to an embodiment of the present invention, the microcapsules (coated particulate matter) have a diameter of 0.5-100 μm. In some embodiments, the particles have a diameter of 0.8-100 μm, in some further embodiments 1-50 μm and in some other embodiments 2-30 μm.

According to certain embodiments of the present invention, the surface of the metal oxide later of the coated particulate matter may be chemically modified by organic groups, in some embodiments hydrophobic groups, attached to its surface.

The hydrophobic groups may be for example an alkyl groups (such alkyl groups may be further substituted with one or more fluoro atoms), aryl groups (such as benzyl or phenyl), and combinations thereof. The groups may be as described below with respect to the process.

In some embodiments the topical medicament comprises tretinoin or its pharmaceutically acceptable salt, hydrate or solvate. Suitable pharmaceutically acceptable salts of the active component(s) (i.e. tretinoin) of this invention include inorganic salts such as: ammonium, alkali metals to include lithium, sodium, potassium, cesium; alkaline earth metals to include calcium, magnesium, aluminium; zinc, barium; or quaternary ammoniums; or organic salts such as arginine, organic amines to include aliphatic organic amines, aromatic amines, t-butylamines, (N-benzylphenethylamine), dicyclohexylamines, dimethylamines, diethanolamines, ethanolamines, ethylenediamines, imidazoles, lysines, methylamines, N-methyl-D-glucamines, N,N'- dibenzylethylenediamines, pyridines, picolinates, piperazines, tris(hydroxymethyl)methylamines, triethylamines, triethanolamines, trimethylamines, or ureas.

In one embodiment, the term "about", refers to a deviance of between 0.0001-5% from the indicated number or range of numbers. In one embodiment, the term "about", refers to a deviance of between 1-10% from the indicated number or range of numbers.

The following examples are presented in order to more fully illustrate the preferred embodiments of the invention. They should in no way, however, be construed as limiting the broad scope of the invention.

EXAMPLES

Example 1

Product 3149 is a combination formulation of encapsulated benzoyl peroxide (E-BPO) 3%, prepared as described in US patent publication 2010-0016443, and encapsulated All Trans Retinoic Acid (E-ATRA) 0.1%, prepared as described in US patent publication US 2012/0202695.

Product 3156 is a combination formulation of similar E-BPO 3% and similar E-ATRA 0.05%.

A clinical trial was designed to assess whether the combination of E-BPO and E-ATRA provides safe and synergistic efficacy as compared to use of either product alone in the treatment of acne vulgaris. Products 3149 and 3156 provide improved outcomes due the stability of the product, as described in US patent publication 2013/0095185, and lead to increased patient compliance.

The purpose of the study was to assess the efficacy, safety, and tolerability of Products 3149 and 3156 in comparison to the individual components, E-BPO 3%, E-ATRA 0.1%, E-ATRA 0.05%, and vehicle (placebo).

This was a randomized, double-blind, multicenter, parallel group, active- and vehicle-controlled study of the efficacy, tolerability, and safety of Products 3149 and 3156 for the treatment of acne vulgaris.

Approximately 720 subjects, age 9 and older, with moderate to severe facial acne (rated 3 or 4 on the 5-point Investigator's Global Assessment [IGA]) were enrolled at up to 37 sites. Participants were randomized 1:1:1:1:1:1 to receive once daily treatment with E-BPO/E-ATRA (3%/0.05%); E-BPO/E-ATRA (3%/0.1%); E-BPO (3%); E-ATRA (0.05%); E-ATRA (0.1%); and vehicle cream. After the screening period, qualified subjects were randomized at the Baseline visit and treated for 12 weeks.

Efficacy assessments included facial lesion counts (inflammatory and non-inflammatory) and IGA assessment ranging from 0 (Clear) to 4 (Severe). Investigators were provided with instructions for lesion counts to ensure consistency of procedure. Patient reported outcomes (PRO) were assessed at Baseline, Weeks 4, 8, and 12 or early termination. Safety was assessed at all visits and included monitoring local and systemic adverse experiences; the Investigator Cutaneous Safety Assessment rating of hyper- and hypopigmentation, erythema and scaling on a scale ranging from 0 (None) to 3 (Severe); and the subject assessment of Local Tolerability rating itching, burning, and stinging on a scale ranging from 0 (None) to 3 (Severe).

Subjects returned to centers for cutaneous safety and local tolerability assessments at Weeks 2, 4, 8, and 12; and IGA and lesion counts were repeated at Weeks 4, 8, and 12. Adverse events and concomitant medications were assessed throughout the treatment period.

All products were supplied in 80-gram pumps (50 g of it is the cream). One pea sized amount was applied on each area of the face (chin, left cheek, right cheek, nose, and forehead) once daily, at bedtime, for 12 weeks.

TABLE 1

Investigator's Global Assessment Scale for Acne Severity

| Score | Grade | Description |
|---|---|---|
| 0 | Clear | Normal, clear skin with no evidence of acne vulgaris |
| 1 | Almost clear | Rare non-inflammatory lesions present, with rare non-inflamed papules (papules must be resolving and may be hyperpigmented, |
| 2 | Mild | Some non-inflammatory lesions are present, with few inflammatory lesions (papules/pustules only; no nodulo-cystic lesions) |
| 3 | Moderate | Multiple Non-inflammatory lesions and, inflammatory lesions are evident: several to many comedones and papules/pustules, and there |
| 4 | Severe | Inflammatory lesions are more apparent, many comedones and papules/pustules, there may or may not be a few nodulo-cystic |

Inflammatory Lesions Definitions

Papule: A small, solid elevation less than 5 mm in diameter. Most of the lesion is above the surface of the skin.

Pustule: A small circumscribed elevation less than 5 mm in diameter that contains yellow-white exudate.

Nodule: An inflammatory lesion greater than or equal to 5 mm in diameter.

Cyst: An inflammatory lesion that contains yellow-white exudate that is greater than or equal to 5 min in diameter.

Non-inflammatory Lesions Definition

Open Comedone (Black head): A lesion in which the follicle opening is widely dilated with the contents protruding out onto the surface of the skin, with compacted melanin cells giving the plug a black appearance.

Closed Comedone (White head): A lesion in which the follicle opening is closed, but the sebaceous gland is enlarged by the pressure of the sebum buildup, which in turn cause the skin around the follicle to thin and become elevated with a white appearance.

TABLE 2

Cutaneous Safety Assessment (Investigator)

| Score | Rating | Definition |
|---|---|---|
| | | Erythema |
| 0 | None | No erythema |
| 1 | Mild | Slight pinkness present |
| 2 | Moderate | Definite redness, easily recognized |
| 3 | Severe | Intense redness |

TABLE 2-continued

Cutaneous Safety Assessment (Investigator)

| Score | Rating | Definition |
|---|---|---|
| | | Scaling |
| 0 | None | No scaling |
| 1 | Mild | Barely perceptible shedding, noticeable only on light scratching or rubbing |
| 2 | Moderate | Obvious but not profuse shedding |
| 3 | Severe | Heavy scale production |
| | | Pigmentation |
| 0 | None | No disturbance of pigmentation |
| 1 | Mild | Barely perceptible pigment change |
| 2 | Moderate | Markedly darker or lighter |
| 3 | Severe | Complete de-pigmentation or severe hyperpigmentation |

TABLE 3

Local Tolerability Scoring (Subject)

| Score | Rating | Definition |
|---|---|---|
| | | Itching |
| 0 | None | No itching |
| 1 | Mild | Slight itching, not really bothersome |
| 2 | Moderate | Definite itching that is somewhat bothersome |
| 3 | Severe | Intense itching that may interrupt daily activities and/or sleep |
| | | Burning |
| 0 | None | No burning |
| 1 | Mild | Slight burning sensation; not really bothersome |
| 2 | Moderate | Definite warm, burning sensation that is somewhat bothersome |
| 3 | Severe | Hot burning sensation that causes definite discomfort and may interrupt daily activities or sleep |
| | | Stinging |
| 0 | None | No stinging |
| 1 | Mild | Slight stinging sensation; not really bothersome |
| 2 | Moderate | Definite stinging sensation that is somewhat bothersome |
| 3 | Severe | Severe stinging sensation that causes definite discomfort and may interrupt daily activities or sleep |

Example 2

Efficacy:

Co-primary efficacy variables were evaluated in this study, and include the following:

Investigator's Global Assessment (IGA)

Lesion count (separately for inflammatory and non-inflammatory)

The co-primary endpoints are:

Proportion of subjects with an assessment of clear or almost clear with at least a 2-grade improvement in IGA at Week 12

Absolute and percent reduction from Baseline in lesion count on the face at Week 12 (separately for inflammatory and non-inflammatory lesions)

Safety:

Safety variables include Investigator Cutaneous Safety Assessment score, subject's tolerability assessment scores, treatment-emergent adverse events (AEs), SAEs, treatment related AEs, AEs leading to study discontinuation, concomitant medications, clinical chemistry, hematology and urinalysis, and ECG evaluation.

Success Criteria:

The following statistical comparisons (both numerically and inferentially) were performed:

Product 3149 (E BPO/E ATRA 3%/0.1%) versus E-BPO 3%, E-ATRA 0.1% and vehicle

Product 3156 (E BPO/E ATRA (3%/0.05%) versus E-BPO 3%, E-ATRA 0.05% and vehicle.

Patient Reported Outcome Questionnaire

The Patient-Reported Evaluation of Facial Acne (PRE-FACE) and Patient Facial Acne Severity Assessment were assessed at study visits 1-6, including screening, baseline, and at Weeks 2, 4, 8, and 12 or early termination (ET), to capture the patient-reported experience of acne vulgaris. The PRE-FACE contains 7-items that constitute two domains. The acne symptom domain (ASD) assesses the severity of acne symptoms (four items) on an 11-point numeric rating scale (NRS) ranging from 0=none to 10=as bad as you can imagine. The acne impact domain (AID) assesses the impacts of acne on the way a patient feels (three items) on an 11-point NRS ranging from 0=not at all to 10=extremely. Higher scores on the Patient Reported Outcome (PRO) questionnaire indicate higher severity of symptoms and impacts associated with acne vulgaris. In addition, the Patient Facial Acne Severity Assessment was assessed along with the PRE-FACE, which is a global item assessing patient-reported overall severity of acne vulgaris on a 5 point verbal rating scale (VRS), ranging from 0 (no acne) to 4 (very severe acne). Respondents were also provided with verbal descriptors to facilitate their ratings.

Results:

TABLE 4

Results for product 3149 at 12 weeks

| Efficacy Results | Product 3149 116 subjects | E-BPO 3% 118 subjects | E-ATRA 0.1% 118 subjects | Vehicle 115 subjects |
|---|---|---|---|---|
| IGA success rate | 39.7% | 22.1% | 31.7% | 12.3% |
| Mean reduction in inflammatory lesions count | 16.9 (64.0%) | 13.8 (49.4%) | 14.9 (57.1%) | 11.5 (42.2%) |
| Mean reduction in non-inflammatory lesions count | 23.6 (53.3%) | 16.2 (37.7%) | 23.8 (57.1%) | 13.7 (32.4%) |

TABLE 5

Results for product 3149 at 4 weeks

| Efficacy Results | Product 3149 116 subjects | E-BPO 3% 118 subjects | E-ATRA 0.1% 118 subjects | Vehicle 115 subjects |
|---|---|---|---|---|
| IGA success rate | 3.1% | 5.4% | 4.85% | 4.5% |
| Mean reduction in inflammatory lesions count | 8.5 (32.8%) | 8.0 (29.3%) | 8.4 (33.2%) | 7.2 (26.3%) |
| Mean reduction in non-inflammatory lesions count | 11.8 (27.6%) | 7.7 (18.4%) | 10.1 (25.9%) | 7.1 (17.9%) |

TABLE 6

Results for product 3149 at 8 weeks

| Efficacy Results | Product 3149 116 subjects | E-BPO 3% 118 subjects | E-ATRA 0.1% 118 subjects | Vehicle 115 subjects |
|---|---|---|---|---|
| IGA success rate | 14.9% | 12.7% | 9.3% | 9.4% |
| Mean reduction in inflammatory lesions count | 13.3 (50.4%) | 9.6 (40.9%) | 12.6 (49.3%) | 9.6 (34.1%) |
| Mean reduction in non-inflammatory lesions count | 18.5 (41.9%) | 10.9 (23.7%) | 18 (43.1%) | 12.0 (29.2%) |

TABLE 7

Results for product 3156 at 12 weeks

| Efficacy Results | Product 3156 117 subjects | E-BPO 3% 118 subjects | E-ATRA 0.05% 118 subjects | Vehicle 115 subjects |
|---|---|---|---|---|
| IGA success rate | 27.4% | 22.1% | 24.9% | 12.3% |
| Mean reduction in inflammatory lesions count | 17.0 (60.8%) | 13.8 (49.4%) | 13.9 (51.7%) | 11.5 (42.2%) |
| Mean reduction in non-inflammatory lesions count | 23.7 (54.9%) | 16.2 (37.7%) | 17.8 (44.6%) | 13.7 (32.4%) |

TABLE 8

Results for product 3156 at 4 weeks

| Efficacy Results | Product 3156 117 subjects | E-BPO 3% 118 subjects | E-ATRA 0.05% 118 subjects | Vehicle 115 subjects |
|---|---|---|---|---|
| IGA success rate | 3.7% | 5.4% | 1.8% | 4.5% |
| Mean reduction in inflammatory lesions count | 9.3 (31.8%) | 8.0 (29.3%) | 7.2 (28.4%) | 7.2 (26.3%) |
| Mean reduction in non-inflammatory lesions count | 11.4 (27.7%) | 7.7 (18.4%) | 6.8 (18.8%) | 7.1 (17.9%) |

TABLE 9

Results for product 3156 at 8 weeks

| Efficacy Results | Product 3156 117 subjects | E-BPO 3% 118 subjects | E-ATRA 0.05% 118 subjects | Vehicle 115 subjects |
|---|---|---|---|---|
| IGA success rate | 13.3% | 12.7% | 8.4% | 9.4% |
| Mean reduction in inflammatory lesions count | 13.5 (48.5%) | 11.7 (40.9%) | 10.5 (39.6%) | 9.6 (34.1%) |
| Mean reduction in non-inflammatory lesions count | 19.1 (45.4%) | 10.9 (23.7%) | 13.0 (32.4%) | 12.0 (29.2%) |

TABLE 10

Results for product 3149 at 2 weeks

| Patient Reported Outcome Results | Product 3149 116 subjects | E-BPO 3% 118 subjects | E-ATRA 0.1% 118 subjects | Vehicle 115 subjects |
|---|---|---|---|---|
| Mean reduction in Acne Symptom Domain (ASD) | 0.72 | 0.53 | 0.69 | 0.49 |
| Mean reduction in Acne Impact Domain (AID) | 1.32 | 0.88 | 0.83 | 0.72 |
| Mean reduction in verbal rating scale (VRS) | 0.1 | 0.2 | 0.1 | 0.3 |

TABLE 11

Results for product 3149 at 4 weeks

| PRO Results | Product 3149 116 subjects | E-BPO 3% 118 subjects | E-ATRA 0.1% 118 subjects | Vehicle 115 subjects |
|---|---|---|---|---|
| Mean reduction in Acne Symptom Domain (ASD) | 1.21 | 0.96 | 1.18 | 0.78 |
| Mean reduction in Acne Impact Domain (AID) | 1.97 | 1.51 | 1.44 | 0.92 |
| Mean reduction in verbal rating scale (VRS) | 0.4 | 0.5 | 0.4 | 0.4 |

TABLE 12

Results for product 3149 at 8 weeks

| PRO Results | Product 3149 116 subjects | E-BPO 3% 118 subjects | E-ATRA 0.1% 118 subjects | Vehicle 115 subjects |
|---|---|---|---|---|
| Mean reduction in Acne Symptom Domain (ASD) | 1.91 | 1.35 | 1.92 | 1.24 |
| Mean reduction in Acne Impact Domain (AID) | 2.65 | 2.09 | 2.36 | 1.44 |
| Mean reduction in verbal rating scale (VRS) | 0.6 | 0.5 | 0.5 | 0.6 |

TABLE 13

Results for product 3149 at 12 weeks

| PRO Results | Product 3149 116 subjects | E-BPO 3% 118 subjects | E-ATRA 0.1% 118 subjects | Vehicle 115 subjects |
|---|---|---|---|---|
| Mean reduction in Acne Symptom Domain (ASD) | 2.72 | 1.97 | 2.57 | 1.44 |
| Mean reduction in Acne Impact Domain (AID) | 3.52 | 2.53 | 3.04 | 1.8 |
| Mean reduction in verbal rating scale (VRS) | 1.0 | 0.8 | 0.9 | 0.6 |

TABLE 14

Results for product 3156 at 2 weeks

| PRO Results | Product 3156 117 subjects | E-BPO 3% 118 subjects | E-ATRA 0.05% 118 subjects | Vehicle 115 subjects |
|---|---|---|---|---|
| Acne Symptom Domain (ASD) | 0.72 | 0.51 | 0.79 | 0.49 |
| Acne Impact Domain (AID) | 1.71 | 0.88 | 1.03 | 0.72 |
| Mean reduction in verbal rating scale (VRS) | 0.4 | 0.2 | 0.2 | 0.3 |

TABLE 15

Results for product 3156 at 4 weeks

| PRO Results | Product 3156 117 subjects | E-BPO 3% 118 subjects | E-ATRA 0.05% 118 subjects | Vehicle 115 subjects |
|---|---|---|---|---|
| Acne Symptom Domain (ASD) | 1.26 | 0.96 | 1.29 | 0.78 |
| Acne Impact Domain (AID) | 2.22 | 1.51 | 1.61 | 0.92 |
| Mean reduction in verbal rating scale (VRS) | 0.6 | 0.5 | 0.4 | 0.4 |

TABLE 16

Results for product 3156 at 8 weeks

| PRO Results | Product 3156 117 subjects | E-BPO 3% 118 subjects | E-ATRA 0.05% 118 subjects | Vehicle 115 subjects |
|---|---|---|---|---|
| Acne Symptom Domain (ASD) | 2.03 | 1.35 | 1.69 | 1.24 |
| Acne Impact Domain (AID) | 3.16 | 2.09 | 2.16 | 1.44 |
| Mean reduction in verbal rating scale (VRS) | 0.8 | 0.5 | 0.6 | 0.6 |

TABLE 17

Results for product 3156 at 12 weeks

| PRO Results | Product 3156 117 subjects | E-BPO 3% 118 subjects | E-ATRA 0.05% 118 subjects | Vehicle 115 subjects |
|---|---|---|---|---|
| Acne Symptom Domain (ASD) | 2.68 | 1.97 | 2.40 | 1.44 |
| Acne Impact Domain (AID) | 3.94 | 2.53 | 2.82 | 1.8 |
| Mean reduction in verbal rating scale (VRS) | 1.1 | 0.8 | 0.8 | 0.6 |

TABLE 18

Results for product 3149 at week 12

| Tolerability Results | Product 3149 116 subjects | E-BPO 3% 118 subjects | E-ATRA 0.1% 117 subjects | Vehicle 116 subjects |
|---|---|---|---|---|
| Erythema | 35 (31.0%) | 24 (20.3%) | 23 (19.8%) | 26 (22.4%) |
| Mild | 18 (15.9%) | 16 (13.6%) | 13 (11.2%) | 19 (16.4%) |
| Moderate | 15 (13.3%) | 8 (6.8%) | 9 (7.8%) | 7 (6.0%) |
| Severe | 2 (1.8%) | 0 (0.0%) | 1 (0.9%) | 0 (0.0%) |
| Scaling | 47 (41.6%) | 21 (17.8%) | 54 (46.6%) | 25 (21.6%) |
| Mild | 37 (32.7%) | 14 (11.9%) | 37 (31.9%) | 23 (19.8%) |
| Moderate | 10 (8.8%) | 7 (5.9%) | 17 (14.7%) | 2 (1.7%) |
| Severe | 0 (0.0%) | 0 (0.0%) | 0 (0.0%) | 0 (0.0%) |
| Burning | 43 (38.1%) | 17 (14.4%) | 41 (35.3%) | 13 (11.2%) |
| Mild | 28 (24.8%) | 15 (12.7%) | 28 (24.1%) | 11 (9.5%) |
| Moderate | 10 (8.8%) | 2 (1.7%) | 11 (9.5%) | 2 (1.7%) |
| Severe | 5 (4.4%) | 0 (0.0%) | 2 (1.7%) | 0 (0.0%) |
| Stinging | 35 (31.0%) | 20 (16.9%) | 35 (30.2%) | 16 (13.8%) |
| Mild | 25 (22.1%) | 13 (11.0%) | 23 (19.8%) | 15 (12.9%) |
| Moderate | 5 (4.4%) | 7 (5.9%) | 10 (8.6%) | 1 (0.9%) |
| Severe | 5 (4.4%) | 0 (0.0%) | 2 (1.7%) | 0 (0.0%) |
| Pigmentation | 15 (13.3%) | 12 (10.2%) | 14 (12.2%) | 17 (14.7%) |
| Mild | 11 (9.7%) | 9 (7.6%) | 10 (8.7%) | 10 (8.6%) |
| Moderate | 4 (3.5%) | 3 (2.5%) | 3 (2.6%) | 7 (6.0%) |
| Severe | 0 (0.0%) | 0 (0.0%) | 1 (0.9%) | 0 (0.0%) |
| Itching | 28 (24.8%) | 22 (18.6%) | 39 (33.6%) | 22 (19.0%) |
| Mild | 20 (17.7%) | 19 (16.1%) | 29 (25.0%) | 19 (16.4%) |
| Moderate | 7 (6.2%) | 3 (2.5%) | 10 (8.6%) | 3 (2.6%) |
| Severe | 1 (0.9%) | 0 (0.0%) | 0 (0.0%) | 0 (0.0%) |

TABLE 19

Results for product 3149 at 12 weeks

| Erythema Results (change in number of adverse events compared to baseline) | Product 3149 116 subjects | E-BPO 3% 118 subjects | E-ATRA 0.1% 117 subjects | Vehicle 116 subjects |
|---|---|---|---|---|
| week 2, N | 111 | 114 | 115 | 114 |
| Mild | −6 | 5 | −2 | 3 |
| Moderate | 4 | −4 | −1 | −5 |
| Severe | 1 | 0 | 0 | 0 |
| week 4, N | 109 | 114 | 106 | 113 |
| Mild | −7 | 0 | −3 | 6 |
| Moderate | −6 | −7 | −11 | −14 |
| Severe | 1 | 0 | 0 | 0 |
| Week 8, N | 102 | 104 | 98 | 110 |
| Mild | −2 | −3 | −11 | 8 |
| Moderate | −5 | −11 | −13 | −13 |
| Severe | 1 | 0 | 0 | 0 |
| Week 12, N | 97 | 101 | 93 | 102 |
| Mild | −15 | −2 | −13 | 0 |
| Moderate | −14 | −14 | −19 | −17 |
| Severe | 0 | 0 | 1 | 0 |

TABLE 20

Results for product 3149 at 2 weeks

| Tolerability Results | Product 3149 116 subjects | E-BPO 3% 118 subjects | E-ATRA 0.1% 117 subjects | Vehicle 116 subjects |
|---|---|---|---|---|
| Erythema | 35 (31.0%) | 24 (20.3%) | 23 (19.8%) | 26 (22.4%) |
| Mild | 18 (15.9%) | 16 (13.6%) | 13 (11.2%) | 19 (16.4%) |
| Moderate | 15 (13.3%) | 8 (6.8%) | 9 (7.8%) | 7 (6.0%) |
| Severe | 2 (1.8%) | 0 (0.0%) | 1 (0.9%) | 0 (0.0%) |
| Scaling | 47 (41.6%) | 21 (17.8%) | 54 (46.6%) | 25 (21.6%) |
| Mild | 37 (32.7%) | 14 (11.9%) | 37 (31.9%) | 23 (19.8%) |
| Moderate | 10 (8.8%) | 7 (5.9%) | 17 (14.7%) | 2 (1.7%) |
| Severe | 0 (0.0%) | 0 (0.0%) | 0 (0.0%) | 0 (0.0%) |
| Burning | 43 (38.1%) | 17 (14.4%) | 41 (35.3%) | 13 (11.2%) |
| Mild | 28 (24.8%) | 15 (12.7%) | 28 (24.1%) | 11 (9.5%) |
| Moderate | 10 (8.8%) | 2 (1.7%) | 11 (9.5%) | 2 (1.7%) |
| Severe | 5 (4.4%) | 0 (0.0%) | 2 (1.7%) | 0 (0.0%) |
| Stinging | 35 (31.0%) | 20 (16.9%) | 35 (30.2%) | 16 (13.8%) |
| Mild | 25 (22.1%) | 13 (11.0%) | 23 (19.8%) | 15 (12.9%) |
| Moderate | 5 (4.4%) | 7 (5.9%) | 10 (8.6%) | 1 (0.9%) |
| Severe | 5 (4.4%) | 0 (0.0%) | 2 (1.7%) | 0 (0.0%) |
| Pigmentation | 15 (13.3%) | 12 (10.2%) | 14 (12.2%) | 17 (14.7%) |
| Mild | 11 (9.7%) | 9 (7.6%) | 10 (8.7%) | 10 (8.6%) |
| Moderate | 4 (3.5%) | 3 (2.5%) | 3 (2.6%) | 7 (6.0%) |
| Severe | 0 (0.0%) | 0 (0.0%) | 1 (0.9%) | 0 (0.0%) |
| Itching | 28 (24.8%) | 22 (18.6%) | 39 (33.6%) | 22 (19.0%) |
| Mild | 20 (17.7%) | 19 (16.1%) | 29 (25.0%) | 19 (16.4%) |
| Moderate | 7 (6.2%) | 3 (2.5%) | 10 (8.6%) | 3 (2.6%) |
| Severe | 1 (0.9%) | 0 (0.0%) | 0 (0.0%) | 0 (0.0%) |

TABLE 21

Results for product 3156 at week 12

| Tolerability Results | Product 3156 117 subjects | E-BPO 3% 118 subjects | E-ATRA 0.05% 120 subjects | Vehicle 116 subjects |
|---|---|---|---|---|
| Erythema | 30 (25.9%) | 24 (20.3%) | 29 (24.2%) | 26 (22.4%) |
| mild | 19 (16.4%) | 16 (13.6%) | 17 (14.2%) | 19 (16.4%) |
| moderate | 10 (8.6%) | 8 (6.8%) | 11 (9.2%) | 7 (6.0%) |
| severe | 1 (0.9%) | 0 (0.0%) | 1 (0.8%) | 0 (0.0%) |
| Scaling | 47 (40.5%) | 21 (17.8%) | 48 (40.0%) | 25 (21.6%) |
| mild | 29 (25.0%) | 14 (11.9%) | 30 (25.0%) | 23 (19.8%) |
| moderate | 16 (13.8%) | 7 (5.9%) | 16 (13.3%) | 2 (1.7%) |
| severe | 2 (1.7%) | 0 (0.0%) | 2 (1.7%) | 0 (0.0%) |
| Burning | 52 (44.8%) | 17 (14.4%) | 41 (34.2%) | 13 (11.2%) |
| mild | 31 (26.7%) | 15 (12.7%) | 23 (19.2%) | 11 (9.5%) |
| moderate | 16 (13.8%) | 2 (1.7%) | 17 (14.2%) | 2 (1.7%) |
| severe | 5 (4.3%) | 0 (0.0%) | 1 (0.8%) | 0 (0.0%) |
| Stinging | 42 (36.2%) | 20 (16.9%) | 31 (25.8%) | 16 (13.8%) |
| mild | 30 (25.9%) | 13 (11.0%) | 23 (19.2%) | 15 (12.9%) |
| moderate | 8 (6.9%) | 7 (5.9%) | 8 (6.7%) | 1 (0.9%) |
| severe | 4 (3.4%) | 0 (0.0%) | 0 (0.0%) | 0 (0.0%) |
| Pigmentation | 16 (13.8%) | 12 (10.2%) | 23 (19.2%) | 17 (14.7%) |
| mild | 13 (11.2%) | 9 (7.6%) | 19 (15.8%) | 10 (8.6%) |
| moderate | 3 (2.6%) | 3 (2.5%) | 4 (3.3%) | 7 (6.0%) |
| severe | 0 (0.0%) | 0 (0.0%) | 0 (0.0%) | 0 (0.0%) |
| Itching | 32 (27.6%) | 22 (18.6%) | 35 (29.2%) | 22 (19.0%) |
| mild | 25 (21.6%) | 19 (16.1%) | 26 (21.7%) | 19 (16.4%) |
| moderate | 6 (5.2%) | 3 (2.5%) | 8 (6.7%) | 3 (2.6%) |
| severe | 1 (0.9%) | 0 (0.0%) | 1 (0.8%) | 0 (0.0%) |

CONCLUSIONS

The above results clearly show synergistic effects of the claimed regimens. For example:

Synergistically lower side effects could be observed in week 12 for product 3149 in scaling, stinging, burning, itching (Table 18), for product 3156 in pigmentation, itching (Table 21).

Synergistically higher efficacy could be observed in week 4 for product 3149 in mean reduction in non-inflammatory lesion count (Table 5), week 8 for product 3149 in IGA success rate, mean reduction in non-inflammatory lesion count (Table 6), in week 4 for product 3156 in reduction in inflammatory and non-inflammatory lesion count (Table 8), week 8 for product 3156 in IGA success rate, mean reduction in inflammatory lesion count, mean reduction in non-inflammatory lesion count (Table 9), in week 12 for product 3156 in mean reduction in inflammatory and non-inflammatory lesion count (Table 7).

Surprisingly, both combinations were found to be significantly better than the single active ingredients. Furthermore, the tolerability and safety of the combination therapy and regimen of the invention was shown to have synergistic effect as compared with each composition administered alone.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method of treating acne comprising: topically applying onto an affected skin area of a subject in need thereof, once a day for a period of time of up to 12 weeks, a topical medicament which consists of the active agents:
   Tretinoin, or a pharmaceutically acceptable salt thereof, in an amount of about 0.05% weight; and
   Benzoyl Peroxide in an amount of about 5% weight.

2. The method according to claim 1, wherein the score of at least one parameter evaluated by an Investigator Cutaneous Safety Assessment is synergistically lower than the score of the parameters evaluated with the same treatment regimen with each of the active agents separately.

3. The method according to claim 2, wherein said at least one parameter evaluated by the Investigator Cutaneous Safety Assessment is selected from erythema, scaling, pigmentation and any combinations thereof.

4. The method according to claim 1, wherein the score of at least one parameter evaluated by a Local Tolerability Score is synergistically lower than the score of the parameters evaluated with the same treatment regimen with each of the active agents separately.

5. The method according to claim 4, wherein said at least one parameter evaluated by the Local Tolerability score is selected from Itching, Burning, Stinging, and any combinations thereof.

6. The method according to claim 1, wherein said topical medicament is a single dose medicament comprising both said active agents.

7. The method according to claim 1, wherein said method reduces at least one of:
   (i) the number of inflammatory acne lesions by at least 50%; or
   (ii) the number of non-inflammatory acne lesions by at least 40%.

8. The method according to claim 7, wherein said method reduces the number of non-inflammatory acne lesions by at least 40%.

9. The method according to claim 7, wherein said method reduces the number of inflammatory acne lesions by at least 50%.

10. The method according to claim 7, wherein said method reduces the number of inflammatory acne lesions by at least 50%; and the number of non-inflammatory acne lesions by at least 40%.

11. The method according to claim 1, wherein said method improves the IGA success rate by at least 20% compared to the baseline score.

12. The method according to claim 1, wherein after two weeks storage at 40° C. of the topical medicament, the concentration of all-trans 5,6-epoxy retinoic acid is lower than 1%.

13. A method according to claim 1, wherein after two weeks storage at 40° C. of the topical medicament, the degradation of said tretinoin is less than 2.5%.

14. The method according to claim 1, wherein said method potentiates the action of tretinoin in the treatment of acne.

15. The method according to claim 1, wherein the release rate of said tretinoin from said topical medicament is less than 60% per h.

16. The method according to claim 1, wherein the release rate of said tretinoin from said topical medicament is less than 60% per h in a medium of 70% IPA (isopropyl alcohol) and 30% water at room temperature.

17. The method according to claim 1, wherein said at least one active agent of said medicament is encapsulated in a shell.

18. The method according to claim 1, wherein both active agents, benzoyl peroxide and Tretinoin, of said medicament are encapsulated in a shell.

19. The method according to claim 18, wherein said shell is an inorganic shell.

20. The method according to claim 19, wherein said shell is a metal oxide or semi-metal oxide inorganic shell.

21. The method according to claim 1, wherein the score of at least one efficacy parameter is synergistically higher than the parameter evaluated with the same treatment regimen with each of the active agents separately.

22. The method according to claim 21, wherein said efficacy parameter is selected from at least one of IGA success rate, mean reduction in inflammatory lesions count, mean reduction in non-inflammatory lesion count, mean reduction in acne symptom domain, mean reduction in acne impact domain and mean reduction in verbal rating scale.

* * * * *